United States Patent [19]

Carlsson et al.

[11] 4,071,510

[45] Jan. 31, 1978

[54] PEPTIDES HAVING A HIGH ADRENOCORTICOTROPIC EFFECT AND A METHOD OF PRODUCING THE SAME

[76] Inventors: Lars Åke Ingemar Carlsson; Jan Louis Mulder, both of Ferring AB, Fack, S-200 60 Malmo 30, Sweden

[21] Appl. No.: 683,144

[22] Filed: May 4, 1976

Related U.S. Application Data

[63] Continuation of Ser. No. 533,403, Dec. 16, 1974, abandoned.

[51] Int. Cl.$^2$ .................... C07C 103/52; A61K 37/00
[52] U.S. Cl. ........................... 260/112.5 R; 424/177
[58] Field of Search ................. 260/112.5 R; 424/177

[56] References Cited

U.S. PATENT DOCUMENTS

| 3,759,891 | 9/1973 | Otsuka et al. | 260/112.5 R |
|---|---|---|---|
| 3,761,459 | 9/1973 | Pless et al. | 260/112.5 R |
| 3,770,715 | 11/1973 | Tesser et al. | 260/112.5 R |
| 3,862,111 | 1/1975 | Low et al. | 260/112.5 R |
| 3,873,510 | 3/1975 | Kisfaludy et al. | 260/112.5 R |
| 3,873,511 | 3/1975 | Otsuka et al. | 260/112.5 R |

OTHER PUBLICATIONS

Geiger et al.; Chem. Abst. 75, 64280x (1971).
Geiger et al.; Chem. Abst. 75, 49596m (1971).

*Primary Examiner*—Delbert R. Phillips
*Attorney, Agent, or Firm*—Ladas, Parry, Von Gehr, Goldsmith & Deschamps

[57] ABSTRACT

The invention concerns peptides having the general formula X—Glu—His—Phe—Arg—Trp—Gly—Lys—Pro—Val—Gly—Lys—Lys—Y—NH$_2$ wherein X represents alkyloxy carbonyl, aryl alkyloxy carbonyl or D-Ser-Met, and Y represents a residue of $n$ diaminomonocarboxylic acids, $n$ being an integer of 2-4, and a method of producing the same.

2 Claims, No Drawings

PEPTIDES HAVING A HIGH ADRENOCORTICOTROPIC EFFECT AND A METHOD OF PRODUCING THE SAME

This is a continuation of appl. Ser. No. 533,403 filed Dec. 16, 1974, now abandoned.

This invention concerns peptides having the general formula

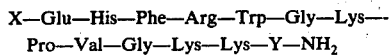
X—Glu—His—Phe—Arg—Trp—Gly—Lys—Pro—Val—Gly—Lys—Lys—Y—NH₂   I wherein X represents alkyloxy carbonyl, aryl alkyloxy carbonyl or D—Ser—Met and Y represents a residue of n diaminomonocarboxylic acids, for instance lysine or ornithine, n being an integer of 2–4.

In particular the invention concerns a method of producing peptides having the general formula I mentioned above, in which a peptide having the general formula

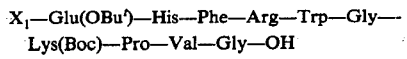
X₁—Glu(OBuᵗ)—His—Phe—Arg—Trp—Gly—Lys(Boc)—Pro—Val—Gly—OH   II wherein Buᵗ represents tertiary butyl, Boc represents tertiary butyloxy carbonyl and X₁ represents alkoxycarbonyl, arylalkyloxy-carbonyl or Boc—D—Ser—Met, is condensed with peptides having the general formula

H—Lys(Boc)—Lys(Boc)—Y—(Boc)ₙ—NH₂   III wherein Boc and Y have the meanings stated above according to methods which are well-known in peptide chemistry, i.e. in the presence of dicyclohexylcarbodiimide, whereupon the protective groups are split off by a strong acid, such as trifluoroacetic acid.

It is a well-known fact that shorter N-terminal ACTH-peptides have an adrenal cortex stimulating effect despite the fact that only the first 18 amino acids, as counted from the N-terminal, are represented. Peptides produced in accordance with the invention and having the general formula I exhibit a biological effect and some of said peptides have a high biological effect; at subcutane tests in mice up to 280 IE/mg. Natural porcine ACTH and most synthetic ACTH-like peptides exhibit an acitivity which is, as a rule, of the order of 100 IE/mg.

On account of their biological properties the peptides produced in accordance with the invention may be administered in small doses for various conditions of illness which means a considerable gain in the form of reduced secondary effects.

It is a further advantage that the ACTH-synthesis which is otherwise quite complicated may be simplified by producing peptides having a reduced size in the peptide chain.

The peptides produced in accordance with the invention have physical and chemical properties which make them suitable for pharmaceutical preparations having a depot effect. According to the invention it is apparent that peptides containing the groups X acting as biological protective groups are not so easily decomposed by the body as other peptides, which, to some extent, explains the obtained depot effect.

The invention will be elucidated below with reference to the following non-restrictive examples.

EXAMPLE 1

A synthesis of N—Cbz—Glu—His—Phe—Arg—Trp—Gly—Lys—Pro—Val—Gly—Lys—Lys—Lys—Lys—NH₂, acetate, aq. (Cbz = carbobenzoxy)

a. 24.0 mmoles of hydrochloric acid gas dissolved in 10 ml of ethyl acetate is added to 3.82 g (6.00 mmoles) Cbz—Glu (OBuᵗ)—His—Phe—Arg—Trp—Gly—Lys(Boc)—Pro—Val—Gly—OH (I) dissolved in 13 ml of dimethylformamide at −10° C and then 0.95 ml (7.20 mmoles) of isoamylnitrite is added. After 15 min neutralization is effected by 3.54 ml (25.3 mmoles) of triethyl amine. To this solution a solution of 4.50 g (5.01 mmoles) of H—Arg—Trp—Gly—Lys(Boc)—Pro—Val—Gly—OH and 0.70 ml (5.00 mmoles) of triethyl amine in 11 ml of dimethylformamide is added at −10° C. After storing in a refrigerator over night the obtained precipitate of triethylammonium chloride is separated and the rest of the solution is evaporated in vacuo. The evaporation residue is treated with ethyl acetate whereby an amorphous powder is formed which will weigh 7.11 g after drying. This product is recrystallized from 64 ml of normal butanol containing 2.5 ml of methanol yielding 5.62 g (75% of the theoretical amount) of blocked decapeptide.

Melting point: 168° C (evolution of gas).

(α)_D²⁵: −50°, c = 0.55 in methanol. Chromatographically uniform with Rf_A: 0.46 and Rf_B: 0.67.

b. Cbz—Glu(OBuᵗ)—His—Phe—Arg—Trp—Gly—Lys(Bpc)—Pro—Val—Gly—Lys(Boc)—Lyc(Boc—Lys(Boc—Lyc(Boc—NH₂. HCl (II)

0.333 mmoles of hydrochloric gas in 0.13 ml of ethyl acetate, 0.372 g (0.400 mmoles) of H—Lys(Boc)—Lys(-Boc)—Lys(Boc)—Lys(Boc)—NH₂, 0.77 g (0.67 mmoles) of N-hydroxysuccinimide and 0.100 g (0.49 mmoles) of N,N′-dicyclohexylcarbodiimide is added to 0.500 g (0.333 mmoles) of (I) dissolved in 3 ml of dimethylformamide. After 48 hours at room temperature the obtained precipitate of N,N′-dicyclohexylurea is separated and the obtained solution is evaporated in vacuo. The evaporation residue is treated with ethyl acetate whereby a voluminous precipitate is formed which weighs 0.870 g after filtering, washing and drying. The product is dissolved in 17 ml of water saturated normal butanol and is extracted with 5×2.5 ml of butanol saturated water. The butanol phase is evaporated in vacuo and the evaporation residue is treated with ether, filtered, washed and dried, whereby 0.620 g of (II) (76% of the theoretical amount) is obtained.

(α)_D²⁵: −34°, c = 0.56 in methanol. Chromatographically uniform with Rf_A: 0.61 and Rf_B: 0.80.

c. Cbz—Glu—His—Phe—Arg—Trp—Gly—Lys—Pro—Val—Gly—Lys—Lys—Lys—Lys—NH₂, acetate, aq.

0.503 g (0.205 mmoles) of (II) is dissolved in a mixture of 2.30 ml trifluoroacetic acid and 0.23 ml of anisole. After 45 minutes at room temperature 15 ml of ether is added whereby a solid white precipitate is obtained which is filtered, washed with ether and dried in vacuo over sodium hydroxide. The product is dissolved in 4 ml of water and is passed through an ion exchanger containing "IRA 400" in acetate form. The water solution is freeze-dried, whereby 0.377 g of a white loose powder is obtained. Chromatographically uniform in system B with Rf_B: 0.07. Low voltage electrophoresis (Millipore Phoroslide system) in a barbiturate buffer of pH 5.0 shows that the product contains traces of impurities which can be removed by column chromatography on carboxymethylcellulose.

EXAMPLE 2

A synthesis of D—Ser—Met—Glu—His—Phe—Arg—Trp—Gly—Lys—Pro—Val—Gly—Lys—Lys—Lys—Lys—NH$_2$, acetate, aq.

a. BOC—D—Ser—Met—Glu (γ—OBu$^t$)—His—Phe—Arg—Trp—Gly—Lys(BOC)—Pro—Val—Gly—OH (I)

0.465 mmoles of hydrochloric acid gas dissolved in 0.190 ml of ethyl acetate is added to 0.055 g (0.155 mmoles) of BOC—D—Ser—Met—N$_2$H$_3$ dissolved in 1 ml of dimethylformamide at −20° C and then 0.021 ml (0.160 mmoles) of isoamylintrite is added. After stirring for 10 minutes at −15° C the solution is neutralized with 0.065 ml (0.465 mmoles) of triethylamine. To this solution a solution of 0.200 g (0.146 mmoles) of Glu (γ—O-Bu$^t$)—His—Phe—Arg—Trp—Gly—Lys—(BOC)—Pro—Val—Gly—OH is added at −15° C in 1 ml of dimethylformamide. The solution is placed in a refrigerator. After 30 minutes in exhibits a pH of 5.5 and so another 0.022 ml (0.160 mmoles) of triethyl amine is added. After storing in a refrigerator over night the formed precipitate of triethylammonium chloride is separated and washed with 2 × 0.5 ml of dimethylformamide. The solution is evaporated to a volume of 2 ml and then dripped into 20 of ethyl acetate. The precipitate which is now formed is separated, washed with 2 × 2 ml of ethyl acetate and air-dried. Quantity: 0.191 g (78 % of the theoretical amount). Melting point: 193° C (evolution of gas). $(α)_D^{25} = 37.4°$, c = 0.36 in methanol. Chromatographically uniform with Rf$_A$: 0.46 and Rf$_B$: 0.70.

b. BOC—D—Ser—Met—Glu—(γ—OBu$^t$)—His—Phe—Arg—Trp—Gly—Lys—Pro—Val—Gly—Lys(BOC)—Lys(BOC)—Lys(BOC)—Lys(BOC)—NH$_2$. HCl (II)

0.110 mmoles of hydrochloric acid gas in 0.037 ml of ethyl acetate, 0.103 g (0.111 mmoles) of H—Lys(BOC)—Lys(BOC)—Lys(BOC)—Lys(BOC)—NH$_2$, 0.230 g (0.200 mmoles) of N-hydroxysuccinimide and 0.226 g (0.110 mmoles) of N,N$^1$-dicyclohexylcarbodiimide is added to 0.181 g (0.107 mmoles) of (I) dissolved in 0.90 ml of dimethylformamide. After 1 week at room temperature the formed precipitate of N,N$^1$-dicyclohexylurea is separated. The solution is evaporated to a volume of 2 ml and then dripped into 15 ml of ethyl acetate during magnetic stirring. The slightly coloured precipitate formed is separated and washed with a total of 10 ml of ethyl acetate. After recrystallization from water saturated normal butanol, 0.247 g (87% of the theoretical amount) of substance is obtained. Melting point: 205° C (evolution of gas). $(α)_D^{24} = 20.8°$, c = 0.36 in dimethylformamide. Rf$_A$: 0.59.

c. D—Ser—Met—Glu—His—Phe—Arg—Trp—Gly—Lys—Pro—Val—Gly—Lys—Lys—Lys—Lys—NH$_2$, acetate, aq.

0.0614 g (0.023 mmoles) of (II) is dissolved in a mixture of 0.40 ml of trifluoroacetic acid and 0.04 ml of anisole. After 40 minutes at room temperature 5 ml of ether is added whereby a solid white precipitate is obtained which is filtered, washed with ether and dried in vacuo over sodium hydroxide. The product is dissolved in 2 ml of water and passed through an ion exchanger with "IRA 400" in acetate form. The water solution is freeze-dried, 0.049 g of substance being obtained.

Chromatography is effected on Merch DC-Fertigplatten Kieselgel F$_{254}$ and in the following solvent systems.

A: normal-butanol: acetic acid: water 4:1:1
B: normal-butanol: pyridine: acetic acid: water 15:10:3:6

What we claim is:
1. Peptides having the general formula X—Glu—His—Phe—Arg—Trp—Gly—Lys—Pro—Val—Gly—Lys—Lys—(Y)$_n$—NH$_2$ wherein X represents ethyloxy carbonyl, benzyloxy carbonyl or D—Ser—Met, and Y represents a residue of a diaminomonocarboxylic acid and n is an integer of 2–4.

2. Peptides accordng to claim 1, wherein the diaminomonocarboxylic acid is lysine or ornithine.

* * * * *